United States Patent
Whayne et al.

(10) Patent No.: US 12,408,906 B1
(45) Date of Patent: Sep. 9, 2025

(54) METHODS AND DEVICES FOR TREATING NEUROPATHIES IN CARDIAC TISSUE

(71) Applicant: Brainwaves Medical, LLC, Durham, NC (US)

(72) Inventors: James G. Whayne, Cary, NC (US); Sidney D. Fleischman, Durham, NC (US)

(73) Assignee: Brainwaves Medical, LLC, Durham, NC (US)

( * ) Notice: Subject to any disclaimer, the term of this patent is extended or adjusted under 35 U.S.C. 154(b) by 0 days.

(21) Appl. No.: 18/340,159

(22) Filed: Jun. 23, 2023

Related U.S. Application Data

(60) Provisional application No. 63/367,047, filed on Jun. 26, 2022.

(51) Int. Cl.
*A61B 17/00* (2006.01)

(52) U.S. Cl.
CPC ............ *A61B 17/00234* (2013.01); *A61B 2017/00247* (2013.01); *A61B 2017/00292* (2013.01)

(58) Field of Classification Search
CPC ........... A61B 2018/00357; A61B 2018/00363; A61B 2018/0038; A61B 2018/00386; A61B 2018/00351; A61M 25/00
See application file for complete search history.

(56) References Cited

U.S. PATENT DOCUMENTS

| | | | |
|---|---|---|---|
| 6,805,128 B1* | 10/2004 | Pless | A61N 1/06 600/459 |
| 7,850,642 B2* | 12/2010 | Moll | A61B 8/4461 604/95.04 |
| 8,430,875 B2* | 4/2013 | Ibrahim | A61B 18/20 606/41 |
| 9,861,802 B2* | 1/2018 | Mickelsen | A61M 25/0169 |
| 10,242,548 B2* | 3/2019 | Dekel | A61B 1/00055 |
| 10,426,545 B2* | 10/2019 | Asirvatham | A61B 18/1492 |
| 10,507,302 B2* | 12/2019 | Leeflang | A61M 25/0113 |
| 11,382,654 B2* | 7/2022 | Lenker | A61M 29/00 |
| 2006/0270900 A1* | 11/2006 | Chin | A61B 1/313 606/1 |
| 2012/0010694 A1* | 1/2012 | Lutter | A61M 25/01 623/1.11 |

(Continued)

OTHER PUBLICATIONS

Jadczyk, T et al. "Stem cell therapy for cardiovascular disease: the demise of alchemy and rise of pharmacology." British journal of pharmacology vol. 169,2 (2013): 247-68. doi:10.1111/j.1476-5381. 2012.01965.x (Year: 2013).*

(Continued)

*Primary Examiner* — Scott J Medway
(74) *Attorney, Agent, or Firm* — Levine Bagade Han LLP

(57) ABSTRACT

Methods, medical systems, and devices for delivering platelet rich plasma, stem cells, exosomes or other extracellular vesicles, growth factors, neuregulins, hormones, extracellular matrix tissue or microvascular tissue fragments allograft, autograft, or xenograft, anti-inflammatories, steroids, and/or other whole, sectioned, particulated, micronized, or otherwise manipulated substances naturally occurring or synthetic that produce, promote, or enhance angiogenesis, reduce inflammation, reduce oxidative stress, promote healing, and/or otherwise reverse neuropathies or improve function of underlying tissues.

6 Claims, 10 Drawing Sheets

(56) References Cited

U.S. PATENT DOCUMENTS

2012/0239069 A1* 9/2012 Benscoter .......... A61B 17/3478
606/185
2017/0020567 A1* 1/2017 Hassett ................ A61B 5/6852

OTHER PUBLICATIONS

Wang, Y et al. "Mesenchymal Stem Cell Therapy Improves Diabetic Cardiac Autonomic Neuropathy and Decreases the Inducibility of Ventricular Arrhythmias." Heart, Lung and Circulation, col. 22,12 (2013): 1018-1025. doi:10.1016/j.hlc.2013.06.007. (Year: 2013).*
Hacking C, Knipe H, Feger J, et al. Pericardial recesses. Reference article, Radiopaedia.org (Accessed on Jan. 31, 2024) https://doi.org/10.53347/rID-54167 (Year: 2017).*
Han, Seongwook & Hwang, Chun. Pericardial Approach for Cardiac Therapies: Old Practice With New Ideas. Korean circulation journal. 40. 479-88. https://doi.org/10.4070/kcj.2010.40.10.479 (Year: 2010).*
Achanta S, et al., "A Comprehensive Integrated Anatomical and Molecular Atlas of Rat Intrinsic Cardiac Nervous System", iScience, 23:101140, Jun. 26, 2020.
Fukuda K, et al., "Cardiac innervation and sudden cardiac death", Circ Res., 116:2005-2019, 2015.
Hadaya, et al., "Autonomic Modulation for Cardiovascular Disease", Frontiers in Physiology, vol. 11, Dec. 22, 2020. doi:10.3389/fphys.2020.617459.
Kimura K, et al., "Development, Maturation, and Transdifferentiation of Cardiac Sympathetic Nerves", Circ Res., 110:325-336, 2012.

* cited by examiner

METHODS AND DEVICES FOR TREATING NEUROPATHIES IN CARDIAC TISSUE

CROSS-REFERENCE TO RELATED APPLICATIONS

This filing claims priority from U.S. Provisional application 63/367,047 entitled, "Renervation to Treat Cardiac Neuropathies," filed Jun. 26, 2022, the contents of which are hereby incorporated by reference in their entirety.

FIELD OF THE INVENTION

The present invention generally relates to intravascular or extravascular medical systems, devices, and methods for delivering platelet-rich plasma, stem cells, exosomes or other extracellular vesicles, growth factors, neuregulins, hydrogels, hormones, human microvascular extracellular matrix tissue or microvascular tissue fragments allograft, autograft, or xenograft, anti-inflammatoiresteroids, and/or other whole, sectioned, particulated, micronized, or otherwise manipulated substances naturally occurring or synthetic that produce, promote, or enhance angiogenesis, reduce inflammation, promote healing, and/or otherwise reverse or improve vascular and neuropathies in cardiac tissues.

Alternatively, the systems, devices, and methods may be used to inject or transfer solutions capable of altering and/or destroying nerve function while preserving adjacent anatomic structures such as ethanol, glutaraldehyde, hydrochloric acid, or other solutions with a pH<3, or other ablative substances that cause denervation in patients with cardiac conditions caused by or exacerbated by neuropathies.

The embodiments of the invention may alternatively target other tissues, such as the myocardium, that interact with the cardiac intrinsic nervous system to improve cardiac function and physiology. The embodiments of the invention may otherwise target the His-Purkinje system, myocardium, or other cardiac tissues regardless of the interaction with the cardiac intrinsic nervous system to improve cardiac function and physiology.

Embodiments of the invention may alternatively deliver devices capable of transmitting radiofrequency energy, cryotherapy, ultrasonic or acoustic shockwave technologies, or other energy-creating modalities to induce improved perfusion of targeted myocardium that is coupled to or otherwise associated with the cardiac intrinsic nervous system. Alternatively, the delivery of therapeutic energy, cryotherapy, or acoustic shockwave technologies may be utilized in a different mode to ablate myocardium associated with the cardiac intrinsic nervous system to reduce the impact of adverse, irreversible neuropathies on heart function and physiology.

More specifically, the invention relates to surgical (open or minimally invasive) or intravascular methods, devices, and apparatus in general, and more particularly to novel injection systems for transporting fluid solutions into fat pads, regions defied by the pericardial reflections, or other areas associated with or influencing heart function and physiology in extravascular spaces, where ganglia, neuronal bodies including intrinsic cardiac neurons, or other nervous system entities reside, to elicit a desired response, whether to encourage angiogenesis, reduce inflammation, otherwise promote healing and correction of neuropathies for reinnervation or repair, healing of nerve function, healing of tissues coupled to or associated with the cardiac intrinsic nervous system, or ablative processes that destroy nerves and/or associated heart tissue for denervation.

BACKGROUND OF THE INVENTION

Many cardiac diseases can directly or indirectly cause or are associated with diseases of the nervous system or neuropathies. Neuropathies result from damaged nerves that typically regulate involuntary physiology, including blood pressure, heart rate, contractility, cardiomyocyte size, or other compensatory mechanisms. In addition, neuropathies and/or coupled myocardial dysfunction may affect timing and synchronization of myocardial contraction by reducing the speed and direction of depolarization and repolarization through the His-Purkinje system. Bodily functions may also be affected by autonomic neuropathies besides cardiac electrophysiology, including body temperature regulation, gastrointestinal function, renal function, bladder control, and sexual performance. Neuropathies also result in chronic pain syndromes.

FIG. 1 illustrates a schematic view of the anatomy and distribution of the cardiac nervous system, including sympathetic 12, parasympathetic 14, and sensory nerves 16 (Kimura K, et al. Development, Maturation, and Transdifferentiation of Cardiac Sympathetic Nerves. Circ Res. 2012; 110:325-336). The cardiac sympathetic 12 nerves extend from sympathetic neurons in the stellate ganglia, which are located bilaterally to the thoracic vertebra (T1, T2, T3). The cardiac parasympathetic nerves 14 extend from parasympathetic neurons in the cardiac ganglia, which are located in the base of both atria of the heart. The sensory nerves 14 project to the upper dorsal horn via dorsal root ganglia. As shown in the transverse section of the heart, the sympathetic nerve fibers are shown within the left ventricle.

Nerve damage impacts biological communication between the heart, blood vessels, various glands, organs, and the brain. Neuropathies can be caused by pre-existing health conditions such as arterial hypertension, diabetes, chronic illnesses such as Parkinson's or HIV, autoimmune disorders, trauma, infections, alcoholism, and injected substances such as medications, chemotherapy agents, illicit drugs, or herbs. While the underlying cause of neuropathies can sometimes be addressed, which allows healing of damaged nerves, localized interventions are frequently needed to encourage healing of the damaged nerves.

Current techniques to address autonomic neuropathies associated with uncontrolled arterial hypertension include renal denervation, where radiofrequency ablation, cryoablation, or other ablative technology is used to eliminate damaged nerves or render damaged nerves nonfunctional to attempt to reduce high blood pressure. While the efficacy of renal denervation has been limited, most likely due to more complex and extensive autonomic neuropathies, sympathectomies have also been performed in attempts to reduce high blood pressure as well as for other conditions. While such attempts at denervation have had some success, the nonspecific and incomplete nature of these approaches, as well as side effects, have limited clinical utilization.

Denervation ablative techniques have also been used to treat atrial fibrillation and other cardiac arrhythmias by destroying ganglionated plexi as well as associated atrial tissue that presumedly serve as triggers or maintenance substrates. Radiofrequency ablation, cryoablation, as well as other ablation techniques, have been used to destroy nerves at locations commonly associated with atrial fibrillation, primarily around the pulmonary veins. While the impact of ganglionated plexi on atrial fibrillation is still under debate, patients with no known structural heart disease and no atrial enlargement likely have autonomic neuropathies commonly resulting from inflammation, oxidative stress, and/or other underlying condition(s) as a contributing culprit.

SUMMARY OF THE INVENTION

The present invention provides intravascular or extravascular (topical or injectable) medical systems/devices for delivering platelet rich plasma, stem cells, exosomes or other extracellular vesicles, growth factors, hydrogels, hormones, human microvascular extracellular matrix tissue or microvascular tissue fragments allograft, autograft, or xenograft, anti-inflammatories, steroids, and/or other whole, sectioned, particulated, micronized, or otherwise manipulated substances naturally occurring or synthetic that produces angiogenesis, reduce inflammation, promote healing and/or otherwise reverse neuropathies (e.g., reinnervation). Embodiments of the invention include novel materials, delivery systems, methods, and processes that induce angiogenesis, provide a scaffold for microvascular to develop, reduce inflammation, or otherwise promote healing to elicit reinnervation of autonomic neuropathies, other nerve dysfunction, and/or underlying myocardial tissue dysfunction, including His-Purkinje damage, to correct, prevent, reduce the severity of, or mitigate risks of cardiac diseases such as uncontrolled, malignant arterial hypertension, atrial fibrillation, supraventricular tachycardias, ischemic coronary artery disease, non-ischemic cardiomyopathies, valvular heart disease, ventricular arrhythmias, right or left bundle branch block, atrioventricular block, or other cardiac condition including those caused by inflammatory diseases and/or oxidative stress capable of causing or associated with microvascular disorders.

Embodiments of the invention also include reinnervation, repair, or healing of nerve function strategies, healing of tissues coupled to or associated with the cardiac intrinsic nervous system. Embodiments of the invention involve novel materials and fluid solution(s), methods, and processes that help alleviate neuropathies resulting from microvascular myocardial damage due to non-cardiac diseases such as diabetes mellitus, kidney disease, pulmonary diseases (pulmonary hypertension, COPD, etc.), and other conditions capable of producing autonomic neuropathies, other nerve dysfunction, and/or underlying myocardial tissue dysfunction, including His-Purkinje damage.

Embodiments of the invention may alternatively be used to inject or transfer fluid solution(s) capable of destroying nerve function while preserving adjacent anatomic structures. Such denervation materials include ethanol, glutaraldehyde, hydrochloric acid or solutions with a pH<3, or other ablative substances that render the targeted nerves inactive. Denervation can render damaged nerves nonfunctional or dysfunction of underlying myocardium to eliminate erratic or atypical signals and address cardiac ailments that result from autonomic neuropathies or other nerve dysfunction.

Embodiments of the invention may comprise a combination of both reinnervation and denervation techniques and materials to define and create a manageable conduction pattern. The way to identify the location (conduction paths) in question and method of access the location may be the same for both techniques.

Embodiments of the invention more specifically relate to surgical (open or minimally invasive) extravascular or percutaneous intravascular methods, devices, and apparatus in general, and more particularly to a novel injection system for transporting fluid solution(s) into fat pads in extravascular spaces or other regions where ganglia, neuronal bodies, or other nerves reside to elicit a desired response, whether to encourage angiogenesis, reduce inflammation, or otherwise promote healing and correction of neuropathies for reinnervation, or ablative processes that destroy nerves for denervation. Embodiments of the invention also involve injecting reinnervation fluid solution(s), powder, hydrogel, or other material directly into the myocardium to encourage angiogenesis and tissue repair or reconstruction, reduce inflammation, or otherwise promote healing along the His-Purkinje system to reverse neuropathies of the cardiac intrinsic nervous system coupled to the His-Purkinje system, improve perfusion and function of the His-Purkinje system, and restore or preserve myocardial function in terms of force, timing, and synchronization of contraction during systole and active filling during diastole.

Surgical extravascular embodiments provide a guiding sheath that can be inserted through a subxiphoid puncture, transdiaphragmatic window, thoracostomy, thoracotomy, median sternotomy, or other surgical access (open or minimally invasive) to the desired region of damaged ganglia, intrinsic cardiac neuronal bodies, other nervous system components, His-Purkinje system, or other myocardial tissue coupled directly or indirectly to the cardiac intrinsic nervous system. The guiding sheath or catheter provides stabilization and a conduit to pass a small diameter, elongated needle and/or lumen guidewire to pass fluid solution(s) designed to cause or encourage reinnervation or denervation.

Percutaneous catheter-based embodiments provide a guiding catheter that can be inserted intravascular and fed to the desired location. The guiding catheter can include a balloon, expanding splines, or other stabilization structure to maintain position while a small diameter, elongated needle is advanced through the vessel wall into the desired location where the reinnervation or denervation fluid solution(s) can be injected.

Percutaneous catheter-based embodiments of the invention that access the epicardial space associated with the pericardial reflections (connective tissue attachments between the pericardium and epicardial heart wall), within which intrinsic cardiac neuronal bodies and other nervous system components reside, include a guiding catheter for passage into the right atrium, and a needle to puncture the interatrial septum inferior to the fossa ovalis to enter the epicardial space adjacent the septum between the right and left atria to access the cavity encapsulated by the pericardial reflections into which the reinnervation (or denervation) fluid solution(s) can be injected to fill the entire pericardial reflection cavity and evoke the desired reinnervation or denervation response. The embodiments of the invention may further include a guidewire with an injection lumen that may be inserted through the needle to pass into the pericardial reflection cavity and provide a more stable access site through which the reinnervation (or denervation) fluid solution(s) can be injected.

Embodiments of the invention may include mechanisms such as electrodes that transmit pulses of radiofrequency (RF) energy, ultrasonic energy (e.g., shockwave therapy), or other energy-creating modality that elicit transient electroporation or other response to the neuronal body membranes, epicardium, and/or other cardiac or nervous system structure to encourage active passing of the fluid solution(s) to their target tissue and promote reinnervation, tissue repair and/or healing. These energy pulses may alternatively be used to cause irreversible electroporation to render tissue (e.g., intrinsic nervous system bodies, underlying myocardium, and/or other tissues) nonfunctional to further denervation procedures.

Embodiments of the invention also include the correction of uncontrolled arterial hypertension by correcting extracardiac neuropathies associated with target ganglia (e.g., celiac ganglia, superior mesenteric ganglion, aorticorenal ganglia, carotid ganglia, etc.) or other associated nervous system components to cause reinnervation. In this application, materials or energy modalities that cause angiogenesis, reduce inflammation, reduce oxidative stress, promote healing, or otherwise correct neuropathies or improve function of associated underlying tissues are injected or delivered through the surgical or intravascular devices into fat pads associated with the ganglia or other neuronal bodies which keep the solution around the ganglia or other neuronal bodies and/or near underlying myocardium or other tissues for a prolonged period of time to maximize the effect of angiogenesis, anti-inflammatory, and/or other healing processes.

Other embodiments of the invention address effects of neuropathies from cardiac diseases, damage to associated myocardial tissues, including the His-Purkinje system, and/or damage to intrinsic cardiac neuronal bodies and/or sympathetic, parasympathetic, or sensory nerves of the heart. In these applications, materials or energy modalities that cause or promote angiogenesis or other processes that correct neuropathies or promote healing of tissues associated with the cardiac intrinsic nervous system are delivered or injected surgically or extravascular during venous catheterization into fat pads associated with nerves that pass alongside coronary vasculature. Alternatively, these materials can be delivered or injected surgically or during catheterization directly into the ventricular septum or ventricular free wall to target nerve components that pass into, through, or along the myocardium and/or the underlying myocardium.

Another embodiment of the invention includes elimination of atrial fibrillation or reversing effects of malignant arterial hypertension, diabetes mellitus, or other disease that affects cardiac function by reversing autonomic neuropathies within the pericardial reflection space by correcting cardiac neuropathies of ganglionated plexi, intrinsic cardiac neuronal bodies, or other nervous system components associated with or adjacent the epicardial atria in fluid communication with the extracardiac space outlined by the pericardial reflections that connect the pericardium to the heart (e.g., atria). In these applications, fluid solution(s) incorporating materials that cause angiogenesis, reduce inflammation, promote healing, or otherwise reverse neuropathies are injected through the surgical or intravascular devices into the extracardiac space associated with the ganglia or other nervous system component(s), which keeps the solution around the ganglia or other nervous system component(s), and/or into contact with underlying cardiac tissue for a prolonged period of time to maximize the effect of angiogenesis, anti-inflammatory, or other healing processes.

The present disclosure includes methods for reversing neuropathies in a heart. For example, such a method can include advancing a piercing structure within a body of a patient and towards the heart; positioning the piercing structure such that a distal end of the piercing structure accesses a cavity defined by one or more pericardial reflections of the heart; delivering a reinnervation material through the piercing structure to fill the cavity defined by the one or more pericardial reflections.

Variations of the methods can include advancing the piercing structure within the body of the patient by navigating a tubular member into the body and advancing the piercing structure through the tubular member.

In another variation, a method under the present disclosure can include positioning the piercing structure by positioning the piercing structure adjacent to an interatrial septum of the heart and penetrating a right atrium of the heart with the piercing structure at a location adjacent to interatrial septum to fill the cavity defined by the one or more pericardial reflections.

Variations of the method can include positioning the piercing structure by positioning the piercing structure adjacent to the one or more pericardial reflections and penetrating at least one pericardial reflection to fill the cavity defined by the one or more pericardial reflections.

In another variation, the method can further include advancing the piercing structure into a myocardium of the heart and delivering the reinnervation material through the piercing structure into the myocardium. Alternatively, a different piercing structure can be advanced into the myocardium.

In another variation, the methods can further include advancing a second elongate structure within a vessel and advancing the piercing structure through a tissue wall in the body and delivering the reinnervation material through both the piercing structure within the heart and through the second elongate structure on an exterior of the heart.

Another variation of a method for reversing neuropathies in a heart can include advancing a piercing structure within a body of a patient and towards the heart; positioning the piercing structure such that a distal end of the piercing structure enters at least one fat pad along an epicardial surface of the heart such that the piercing structure accesses one or more nerve members along a coronary vasculature; passing a guidewire through the piercing structure into the at least one fat pad, wherein the guidewire comprises a lumen; delivering a reinnervation material through the lumen of the guidewire such that the reinnervation material contacts the one or more nerve members.

The methods can further include advancing a second elongate structure within a vessel and advancing the guidewire through a tissue wall in the body, and delivering the reinnervation material through both the guidewire within the heart and through the second elongate structure on an exterior of the heart.

In another variation, the method can further include advancing a second elongate structure within a vessel and advancing the piercing structure through a tissue wall in the body, and delivering the reinnervation material through both the piercing structure within the heart and the second elongate structure on an exterior of the heart.

The present disclosure also includes systems for delivering a reinnervation material into a cardiac tissue to reverse neuropathies. For example one variation of a system includes a handle; an elongate shaft extending from a distal end of the handle, the elongate shaft having a distal portion configured to be steerable; a steering actuator on the handle, the steering actuator operatively coupled to the distal portion to control steering of the distal portion; a guidewire extending at least partially through the elongate shaft, such that the guidewire is extendable from a far end of the distal portion, the guidewire having a lumen extending therethrough and at least one opening to deliver the reinnervation material from the lumen to the cardiac tissue; and a connector configured to fluidly couple a source of the reinnervation material to the lumen of the guidewire.

Variations of the system can further include a piercing structure at a far end of the distal portion, where the guidewire is advanceable through the piercing structure. The piercing structure can be fixed or axially advanceable out of the elongate shaft.

The piercing structure can include a plurality of openings to permit delivery of the reinnervation material into the cardiac tissue. The guidewires described herein can include a guidewire having a sharp tip.

Moreover, the far end of the distal portion can be configured to advance the guidewire at an angle relative to an axis of the elongate shaft. Alternatively, or in combination, the far end of the distal portion can be configured to advance the guidewire distally in alignment with an axis of the elongate shaft.

Variations of the system includes a first magnetic structure on a distal section of the guidewire and a second magnetic structure on a distal section of the second elongate member.

BRIEF DESCRIPTION OF THE FIGURES

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION

Figure 1:
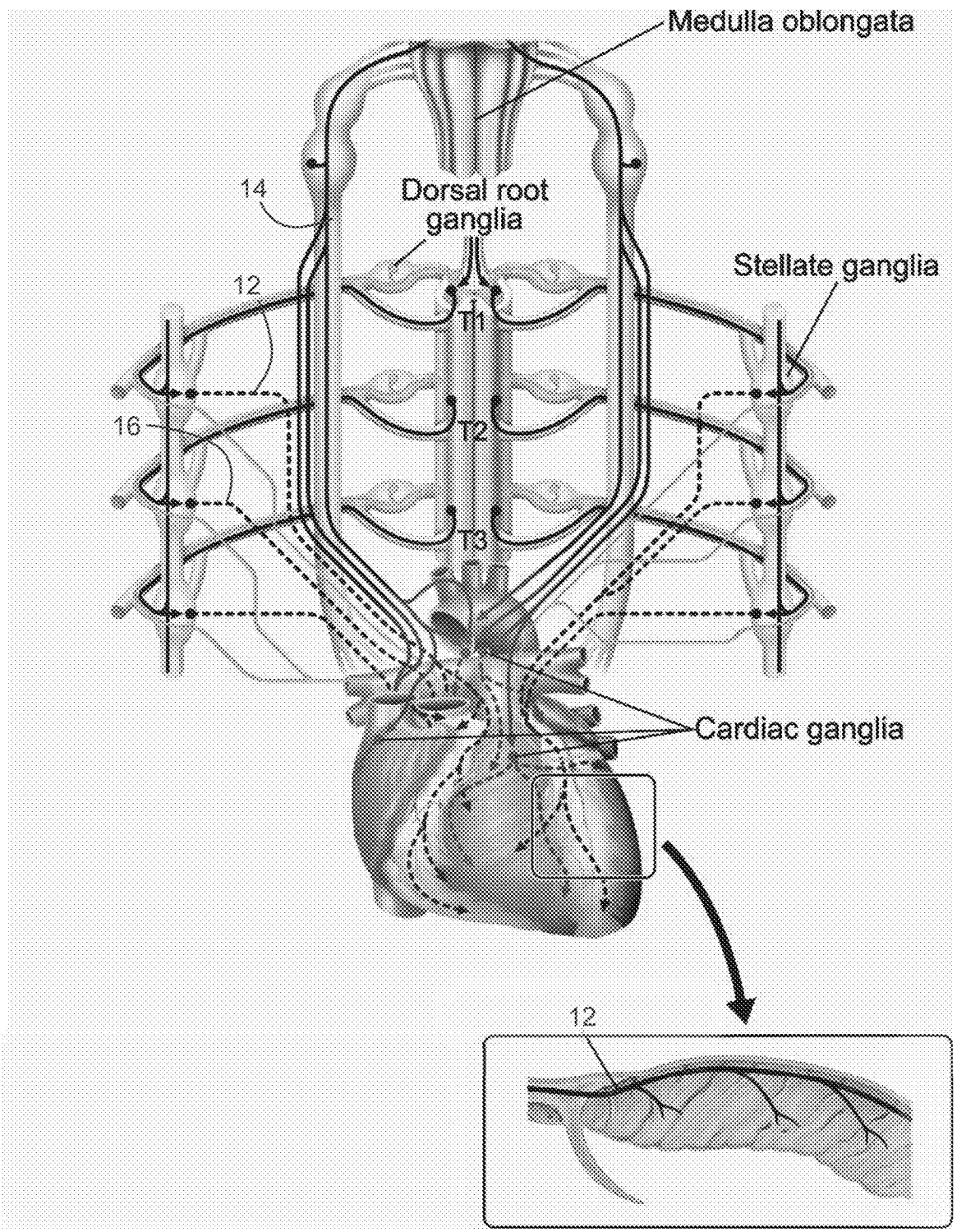
FIG. 1 is a schematic view showing the anatomy and distribution of the cardiac nervous system, including sympathetic, parasympathetic, and sensory nerves. (Kimura K, et al. Development, Maturation, and Transdifferentiation of Cardiac Sympathetic Nerves. Circ Res. 2012; 110:325-336)

The present disclosure provides methods, devices, and systems, either intravascular or extravascular, for delivering platelet-rich plasma, stem cells, exosomes or other extracellular vesicles, growth factors, hormones, neuregulins, hydrogels, human microvascular tissue allograft, extracellular matrix tissue, or microvascular tissue fragments allograft, autograft, or xenograft, anti-inflammatoiresteroids, and/or other whole, sectioned, particulated, micronized, or otherwise manipulated substances or fluid solution(s) including novel therapeutics naturally occurring or synthetic that produce angiogenesis, reduce inflammation, promote healing, or otherwise reverse neuropathies (e.g. reinnervation materials) or improve vascular and neuropathies in cardiac tissues.

The ability to reverse or repair neuropathies (e.g., reinnervation) and/or improve function and performance of tissues coupled to or associated with cardiac intrinsic nervous system helps correct, prevent, reduce the severity of, or mitigate risks of cardiac diseases such as uncontrolled, malignant arterial hypertension, atrial fibrillation, supraventricular tachycardias, ischemic coronary artery disease, non-ischemic cardiomyopathies, valvular heart disease, ventricular arrhythmias, right or left bundle branch block, atrioventricular block, or other cardiac condition including inflammatory diseases, oxidative stress, and/or other mechanisms capable of causing or associated with microvascular tissue deficiencies and/or disorders causing autonomic neuropathies, or other nerve damage or dysfunction.

The ability to cause reinnervation helps correct injury caused by cardiac diseases such as uncontrolled, malignant arterial hypertension, atrial fibrillation, supraventricular tachycardias, ischemic coronary artery disease, non-ischemic cardiomyopathies, valvular heart disease, ventricular arrhythmias, right and left bundle branch block, atrioventricular block, or other cardiac condition including inflammatory diseases capable of causing or associated with microvascular disorders causing autonomic neuropathies, other nerve damage or dysfunction, or damage to underlying tissues coupled to or associated with neuronal bodies. Embodiments of the invention also help alleviate neuropathies resulting from microvascular myocardial damage due to non-cardiac diseases such as diabetes mellitus, kidney disease, pulmonary diseases (pulmonary hypertension, COPD, etc.), and other conditions capable of producing autonomic neuropathies or other nerve dysfunction.

The present invention includes variations of methods, devices, and systems that include reinnervation strategies, novel materials, fluid solution(s), powders, hydrogels, methods, and processes that help alleviate neuropathies or repair or help heal dysfunctional tissues coupled to or associated with neuronal bodies resulting from microvascular myocardial damage due to diseases such as diabetes mellitus, kidney disease, pulmonary diseases (pulmonary hypertension, COPD, etc.), and other conditions capable of producing autonomic neuropathies or other nerve dysfunction.

In additional variations of the methods, systems, and devices can inject or transfer fluid solution(s) capable of destroying nerve function while preserving adjacent anatomic structures such as ethanol, glutaraldehyde, hydrochloric acid, other solution with a pH<3, or other ablative substances that cause denervation of neuropathies or dysfunction of underlying myocardium. This denervation can render damaged nerves or myocardium coupled to or associated with damaged neuronal bodies, nonfunctional to eliminate erratic or atypical signals and address cardiac ailments that result from autonomic neuropathies or other nerve dysfunction.

In one variation, elongated structures (e.g. catheters) are used, where the structures contain at least one electrode or other energy transmission member(s) that transmit pulses of radiofrequency (RF) energy, ultrasonic energy (e.g. shockwave therapy), or other energy-creating modality that elicit transient electroporation or other response to the neuronal body membranes, epicardium, and/or other cardiac or nervous system structure to encourage active passing of the fluid solution(s) to their target tissue and promote reinnervation, tissue repair and/or healing. These energy pulses may alternatively be transmitted into targeted neuronal bodies, underlying myocardium, or other targeted tissue(s) to directly cause irreversible electroporation to render tissue (e.g., intrinsic nervous system bodies, underlying myocardium, and/or other tissues) nonfunctional to enhance or enable denervation procedures.

Variation of the inventions described herein can specifically relate to surgical extravascular or percutaneous intravascular methods, devices, and apparatus in general, and more particularly to an injection system for transporting fluid solution(s) into fat pads or other extravascular spaces where ganglia or other neuronal bodies reside to elicit a desired response, whether to encourage angiogenesis, reduce inflammation, impact oxidative stress, promote healing, or otherwise correct or repair neuropathies or underlying tissue coupled to or associated with neuronal bodies for reinnervation, or ablative processes that destroy nerves or underlying tissue coupled to or associated with neuronal bodies for denervation.

One variation of the treatments described herein includes correction of uncontrolled arterial hypertension by reversing/healing cardiac neuropathies (e.g., reinnervation) associated with target ganglia (e.g., celiac ganglia, superior mesenteric ganglion, aorticorenal ganglia, carotid ganglia, etc.) in proximity to and/or in association with the vasculature outside the heart. Alternatively, underlying tissues that are coupled to, are associated with, or affect the function of the cardiac intrinsic or extrinsic nervous system may be targeted to improve function of the neuronal bodies and the associated tissues and improve the interaction between neuronal bodies and underlying tissues.

Additional representative applications involve administering reinnervation materials and/or fluid solution(s) into heart regions in which ganglia, cardiac intrinsic neurons, or other neuronal bodies reside and are contained within encapsulated fat pads, interconnective tissue, or other tissues. These applications include correction of atrial fibrillation; mitigation of sympathetic, parasympathetic, and/or sensory neuropathies in myocardial infarction, congenital disorders, diabetes mellitus, and/or other chronic diseases; improved synchronization and/or timing of heart wall electrophysiologic conduction by reversing neuropathies associated with the vagal nerves, cardiac intrinsic nervous system coupled to or associated with the His-Purkinje system, or other intracardiac neuronal bodies, and/or other clinical conditions impacted by neuropathies of the heart. The applications may also improve perfusion and function of tissues, including myocardium, that are coupled to or associated with the cardiac nervous system, such as the His-Purkinje system.

Variations of the treatment applications, materials, and/or fluid solution(s) that cause angiogenesis, reduce inflammation, reduce oxidative stress, promote healing, or other processes that reverse neuropathies or improve function of tissues coupled to or associated with cardiac intrinsic nervous system are injected through surgical or intravascular device embodiments of the invention into the fat pads associated with or in proximity to the ganglia, cardiac intrinsic neurons, and/or other neuronal bodies. Injecting angiogenic-inducing fluid solution(s) or material designed to elicit other response that repairs, heals, or otherwise improves function of neuronal bodies or tissues coupled to or associated with neuronal bodies into fat pads and/or interconnective tissues that surround the ganglia/nerves keeps the solution in contact with the ganglia/nerves for a prolonged period of time to maximize diffusion, osmosis, or other mechanism that exposes neuronal bodies to substances that elicit angiogenesis, reduce inflammation, reduce oxidative stress, or other processes capable of healing/reversing neuropathies or restore function of underlying tissues coupled to or associated with neuronal bodies.

The reinnervation materials and/or fluid solution(s) of the invention may be injected into fat pads and/or tissues coupled to or associated with the intrinsic cardiac nervous system (ICNS), which contains parasympathetic, sympathetic, and sensory neuronal bodies as shown in FIG. 1. (Kimura K, et al. Development, Maturation, and Transdifferentiation of Cardiac Sympathetic Nerves. Circ Res. 2012; 110:325-336.) In particular, fat pads along the coronary arteries along may be targeted where nerves (sympathetic, parasympathetic, and/or sensory) are associated with myocardium. Neuropathies of the cardiac intrinsic nervous system in patients with cardiac diseases, including coronary artery disease with prior myocardial infarction and congenital development disorders, may produce an imbalance in sympathetic innervation, while chronic diseases such as diabetes mellitus may cause denervation of the cardiac sensory nerves, all of which can lead to cardiac arrhythmias and sudden cardiac death. (Fukuda K, et al. Cardiac innervation and sudden cardiac death. Circ Res. 2015; 116:2005-2019.) Reversing neuropathies associated with or improving function of underlying tissues coupled to the intrinsic cardiac nervous system (ICNS) can mitigate risks from unbalanced neuronal body activities of the sympathetic, parasympathetic, and sensory nervous systems.

Figure 5:
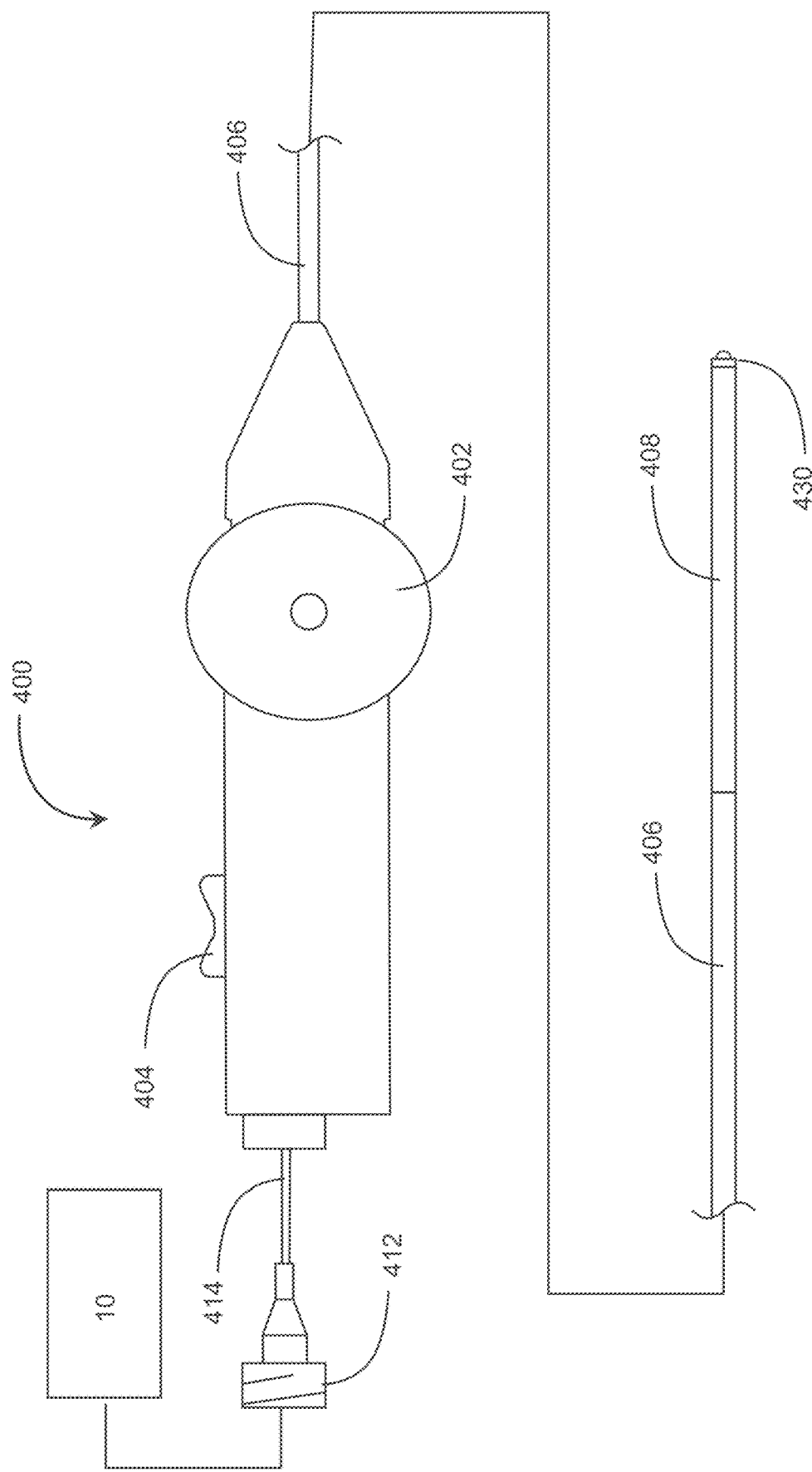
FIG. 5 illustrates an example of a guiding catheter or sheath for use in delivering the reinnervation substances.

Reinnervation materials and/or solution(s) may be injected into fat pads and/or other tissues along the epicardial space that is encapsulated by the pericardial reflections where gangionated plexi (e.g. right ventricular ganglionated plexus, right atrial ganglionated plexus, ventral septal ventricular ganglionated plexus, cranial medial ventricular ganglionated plexus, left atrial ganglionated plexus, dorsal atrial ganglionated plexus, inferior vena cava-inferior atrial ganglionated plexus, or other GPs), intrinsic cardiac neurons, or other neuronal bodies coupled to the heart at known published anatomic locations. (Hadaya, et al. Autonomic Modulation for Cardiovascular Disease. Frontiers in Physiology. 2020 Dec. 22. doi: 10.3389/fphys.2020.617459) (Achanta S, et al. A Comprehensive Integrated Anatomical and Molecular Atlas of Rat Intrinsic Cardiac Nervous System. iScience. 2020 Jun. 26; 23:101140.) FIG. 5 shows a posterior view of the heart, illustrating common locations for ganglionated plexi, or other neuronal bodies impacting the cardiac nervous system.

Figure 2A:
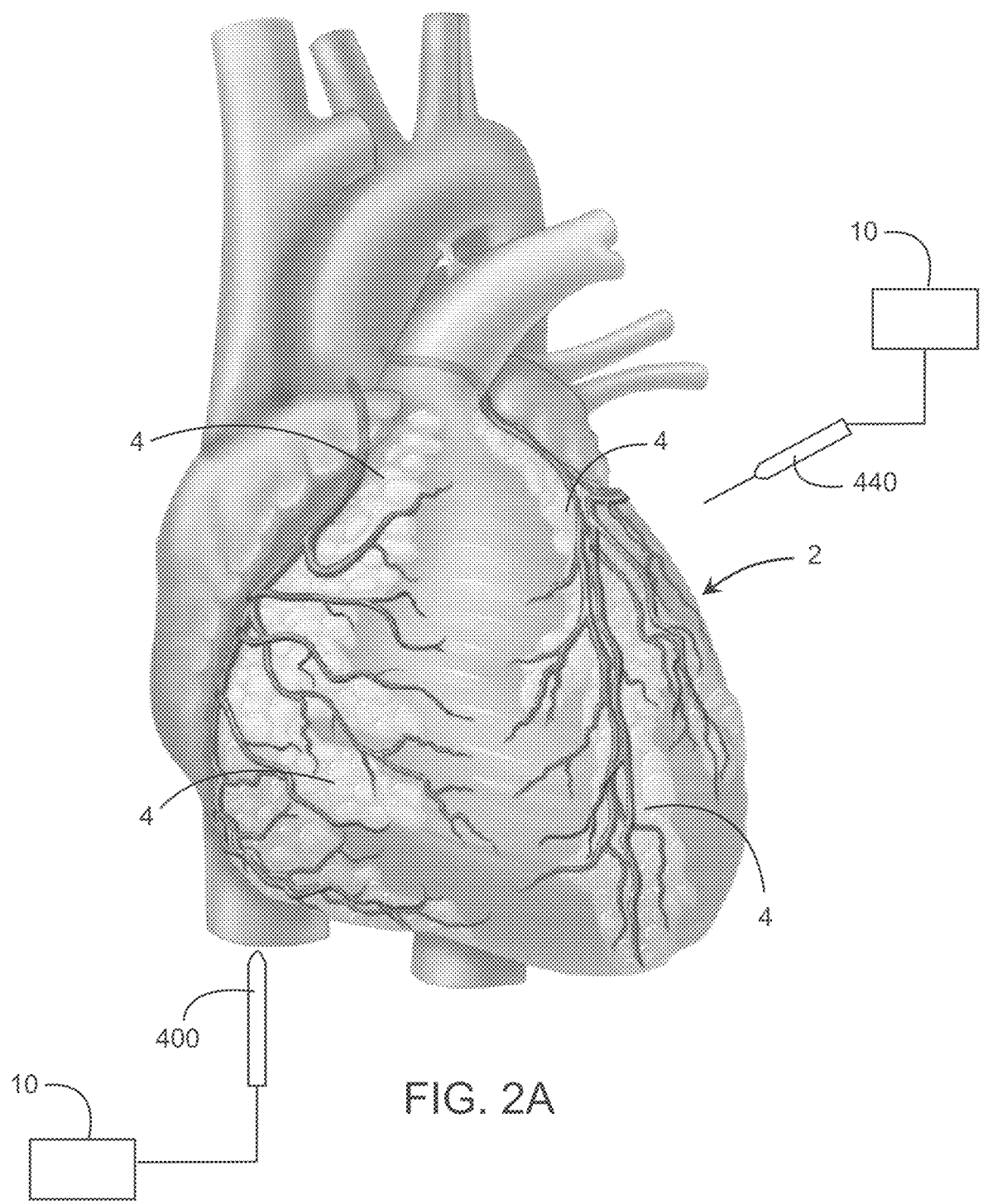
FIG. 2A shows a perspective view of the heart and fat pads along the coronary microvasculature.
Figure 2B:
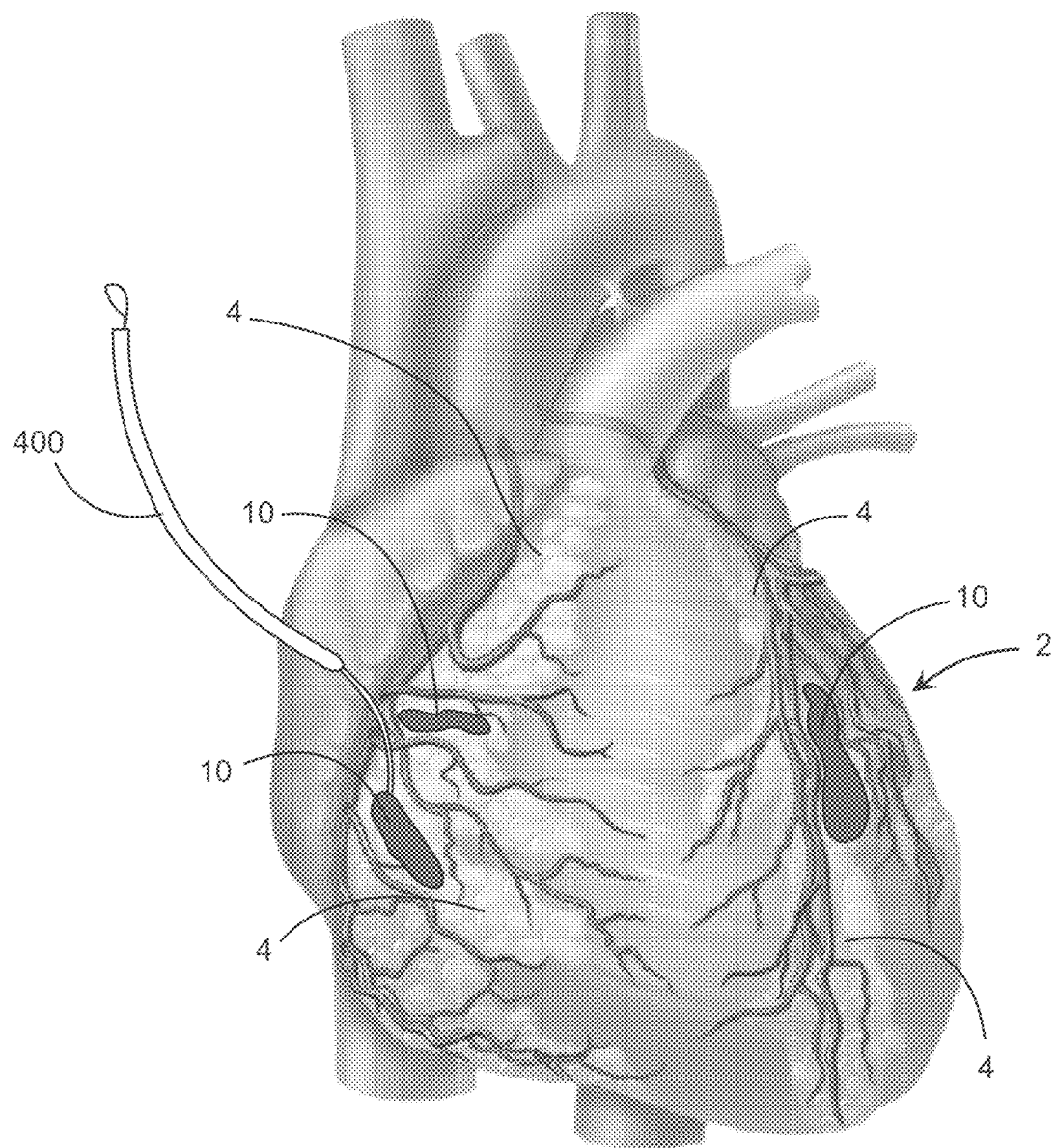
FIG. 2B shows a perspective view of the heart with reinnervation material and/or fluid solution(s) injected into the fat pads.

FIG. 2A illustrates a perspective view of a heart 2 showing fat pads 4 along the coronary microvasculature (i.e., arteries and veins), along which neuronal bodies traverse. FIG. 2A also illustrates the use of either a catheter 400 or needle 440 to deliver the angiogenic-inducing materials 10, as discussed herein. It is also noted that treatment can occur via thoracoscopic, endoscopic, or open surgery. FIG. 2B shows a perspective view of the heart of FIG. 2A to demonstrate an example where the reinnervation material 10 and/or fluid solution(s) 10 was injected into fat pads 4 associated with cardiac neuronal bodies. While the figure illustrates a sheath or catheter 400 used for the injection, injection of the reinnervation material 10 can occur via percutaneous, intravascular or surgical, or extravascular approaches.

Figure 3:
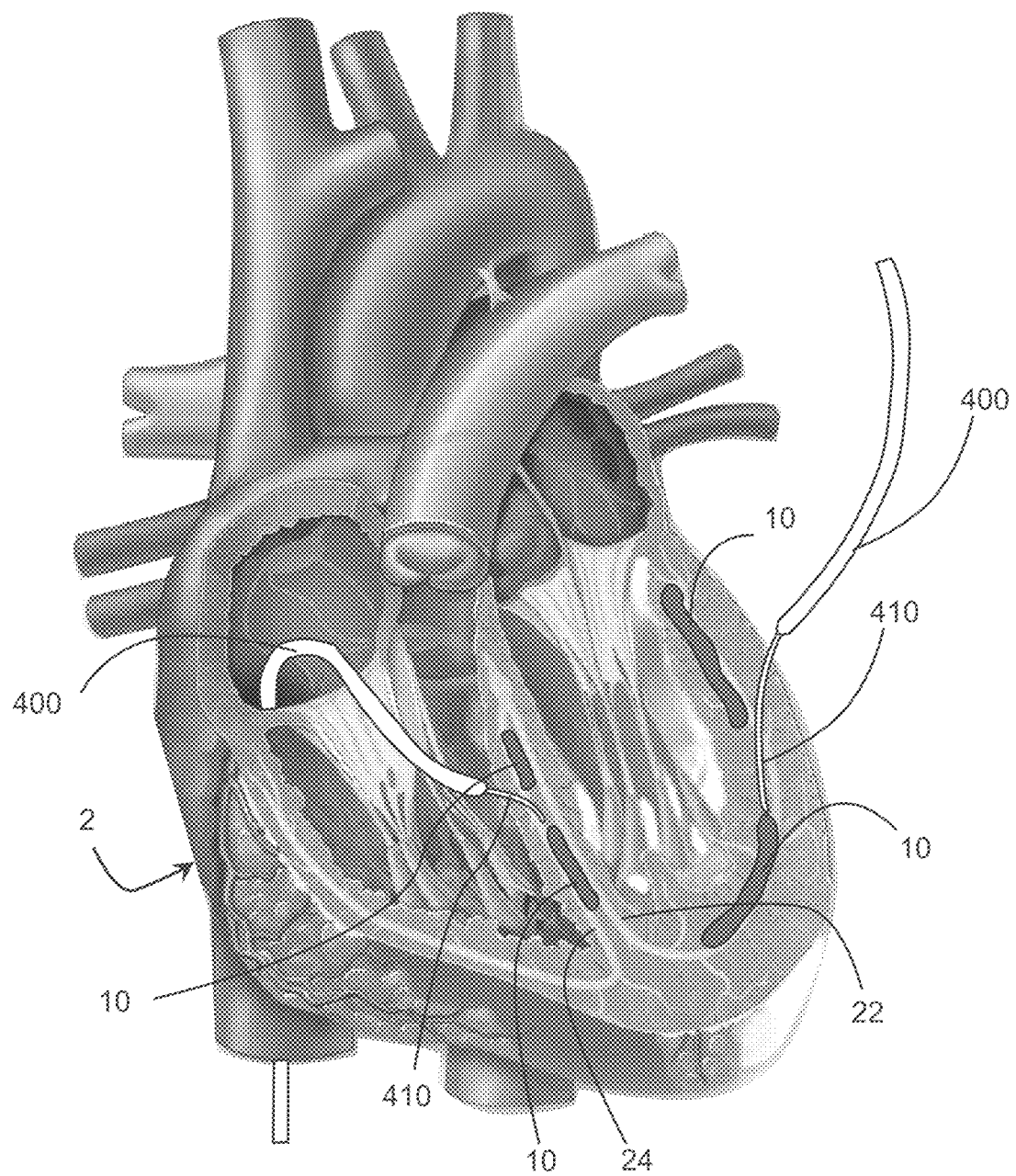
FIG. 3 shows a side-sectional view of the heart showing the Sino-atrial node, atrioventricular node, atrial neuronal bodies, and His-Purkinje system of the heart with reinnervation material delivered into tissue.

FIG. 3 shows a side-sectional view of the heart 2 showing the Sino-atrial node, atrioventricular node, atrial neuronal bodies, and His-Purkinje system of the heart with reinnervation material and/or fluid solution(s) injected into myocardium. FIG. 3 illustrates reinnervation material and/or fluid solution(s) 10 injected into myocardium associated with the His-Purkinje system.

Figure 4A:
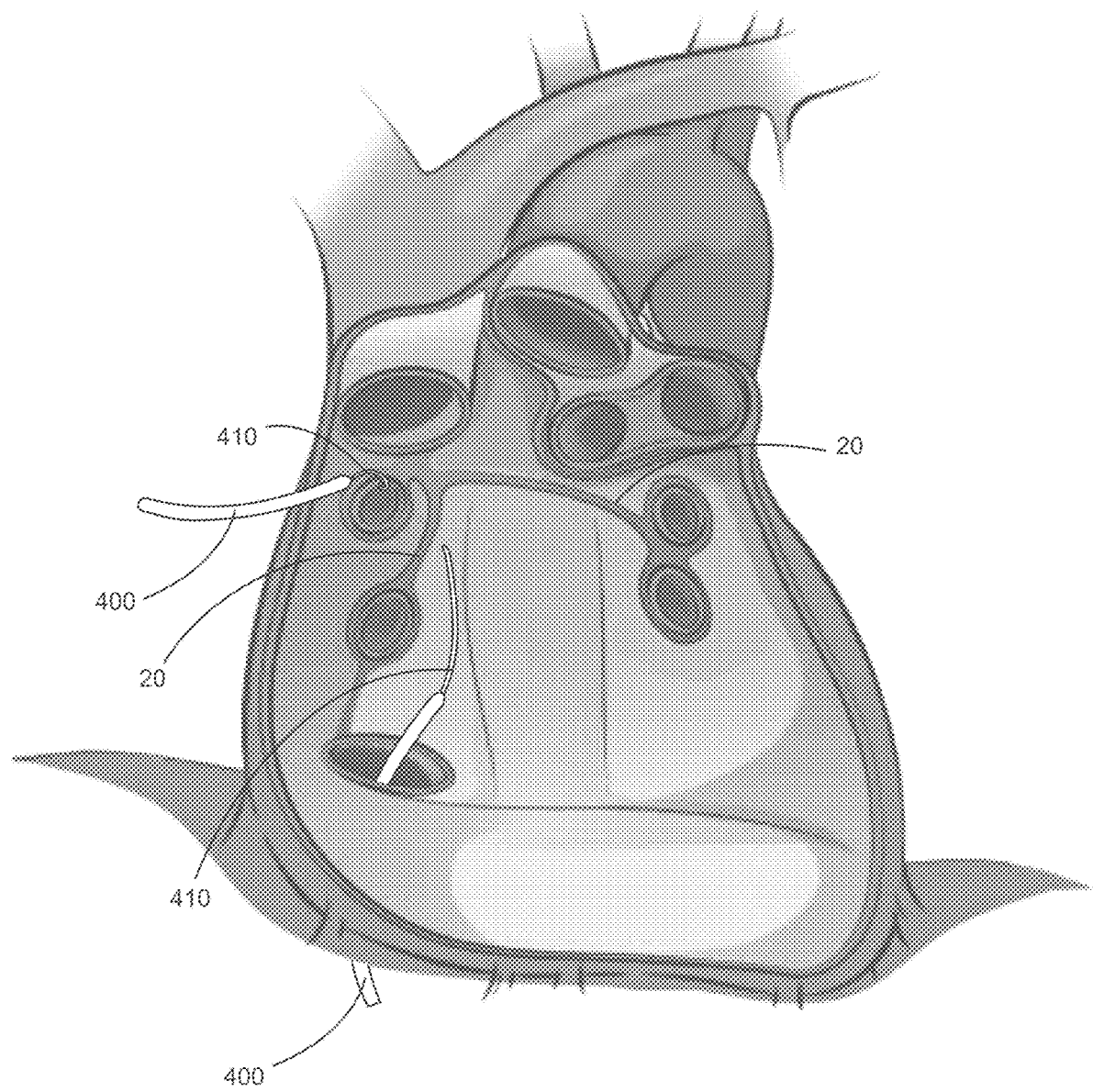
FIG. 4A illustrates devices that can either access cavities defined by the pericardial reflections in either a percutaneous approach (e.g., through a vessel) or an extravascular or surgical approach.
Figure 4B:
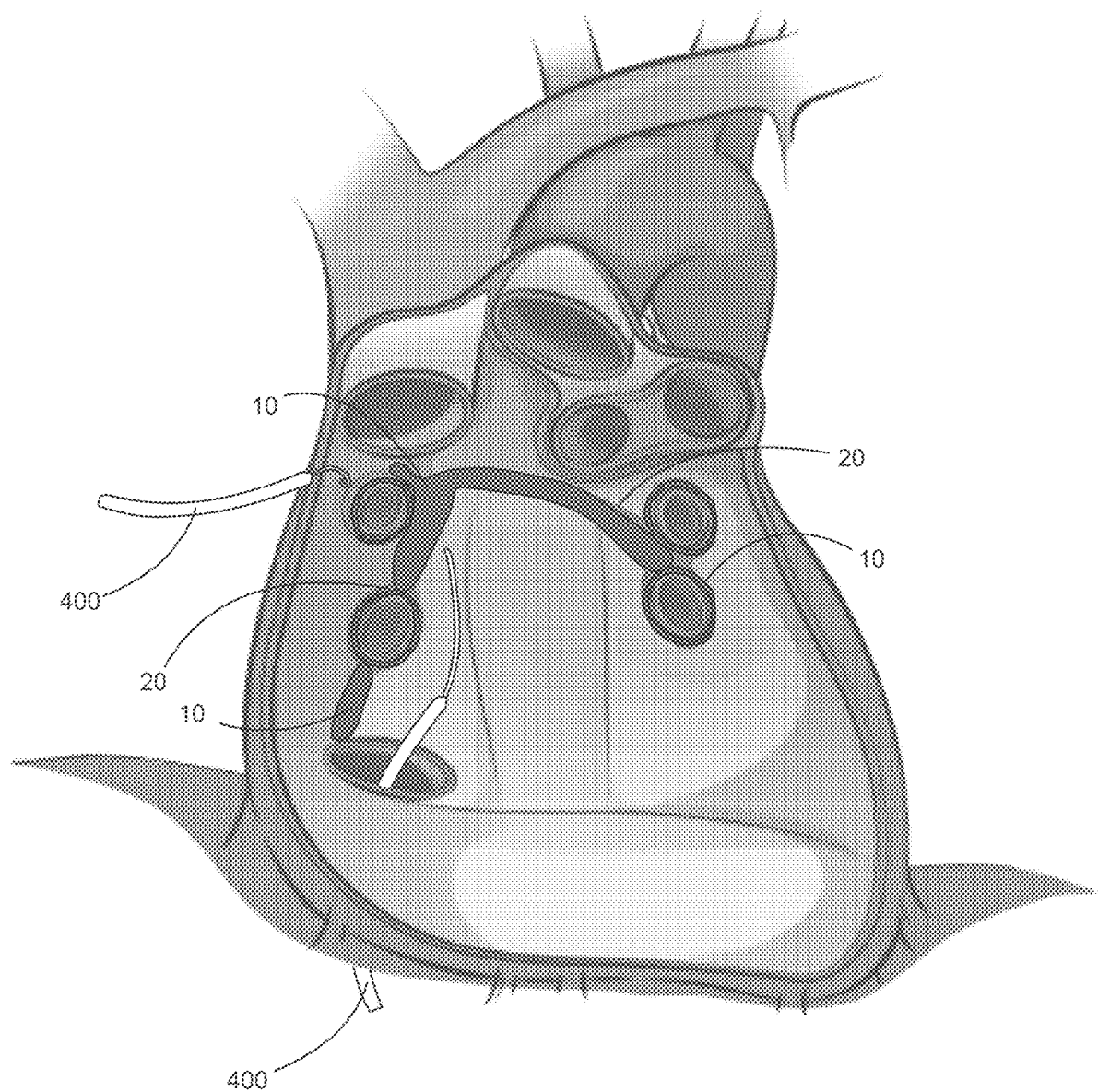
FIG. 4B illustrates reinnervation material and/or fluid solution(s) injected into myocardium in the cavities defined by the pericardial reflections, where ganglionated plexi and/or other neuronal bodies reside, are coupled with and/or are adjacent.

FIG. 4A illustrates a cardiac surface with the vessels removed to highlight the pericardial reflections 20 that define cavities. As shown, treatment devices 400 can access the region through a vascular or extravascular approach. FIG. 4B illustrates reinnervation material 10 and/or fluid solution(s) 10 injected into myocardium in the cavities defined by the pericardial reflections, where ganglionated plexi and/or other neuronal bodies reside, are coupled with, and/or are adjacent.

Injecting angiogenic-inducing materials into fat pads located within or adjacent the pericardial reflections as shown in FIGS. 4B, which connects the heart, including the atria and great vessels, to the pericardium, has the potential to eliminate atrial fibrillation, improve AV node function, improve atrial and/or ventricular synchrony, balance the sympathetic and parasympathetic nervous systems, ensure sensory nerve function, or other clinical application by correcting cardiac neuropathies of ganglionated plexi, intrinsic cardiac nervous system, cardiac autonomic nervous system, vagal nervous system, or other neuronal bodies. In addition, underlying tissue (e.g., myocardium) coupled to or associated with the cardiac intrinsic nervous system such as atrial myocardium, ventricular myocardium, and the His-Purkinje system may be affected to improve performance of heart tissue and interaction between the cardiac intrinsic nervous system and myocardium. In this, as well as other applications, ganglia or other neuronal bodies along the epicardial atria and/or great vessels are targeted for reinnervation by injecting reinnervation materials and/or solution(s) within the extracardiac space defined by the pericardial reflections that connect the pericardium to the atria and the great vessels.

In the variation shown in FIG. 4B, that injects reinnervation materials 10 and/or fluid solution(s) 10 into encapsulated regions defined by the attachments between the pericardium and the atria and great vessels that are associated with fat pads that house or are adjacent to ganglionated plexi or other neuronal bodies produce, promote, or enhance angiogenesis, reduce inflammation, reduce oxidative stress, promote healing, or otherwise correct neuropathies or improve function of underlying myocardium. To accomplish a reinnervation procedure, surgical or intravascular devices are inserted into the extracardiac space defined by the pericardial reflections, which are associated with the ganglia/nerves and underlying cardiac tissue. The reinnervation material and/or solution(s) are injected into the encapsulated space defined by the heart, pericardium, and pericardial reflections that surround the ganglia/nerves such that the reinnervation material and/or solution(s) remain in contact with the target neuronal bodies and underlying cardiac tissue for a prolonged period of time to maximize the effect of angiogenesis, anti-inflammatory, healing, and/or other reinnervation processes.

Surgical access may be attained through direct injection via a needle or lumen guidewire inserted surgically via subxiphoid pericardiocentesis, subxiphoid pericardial window, thoracoscopy, thoracotomy, median sternotomy, or other extracardiac and extravascular approach. Surgical extravascular embodiments provide a guiding sheath 400 that can be inserted through a subxiphoid puncture, transdiaphragmatic window, thoracostomy, thoracotomy, median sternotomy, or other surgical access to the desired region of damaged ganglia, neuronal bodies, other nerves, and/or underlying cardiac tissues (See e.g., FIG. 4A). The guiding sheath 400 provides stable position and a conduit to pass a piercing structure such as a small diameter, elongated needle and/or injection guidewire 410 to pass the fluid solution(s) to fill the cavity defined by the pericardial reflections to cause reinnervation or denervation of the ganglionated plexi, other neuronal bodies, and/or underlying cardiac tissues. Clearly, the piercing structure can be any structure that pierces tissue and optionally allows for delivery of the therapeutic substances.

Surgical or percutaneous catheter-based variations of the treatments described herein can be utilized to inject reinnervation materials and/or fluid solution(s) that induce angiogenesis, reduce inflammation, reduce oxidative stress, or otherwise promote healing directly into the myocardium, including along the septum between the right and left ventricles of the heart to target the His-Purkinje system 22, 24 shown in FIG. 3. In these variations, a needle (as described below) provides a passage so an infusion device (e.g., an infusion guidewire or other catheter) 410 can be inserted directly into the myocardium adjacent the His-Purkinje system 22 24 components to inject angiogenic-inducing materials or solutions 10. Alternatively, the reinnervation materials and/or fluid solution(s) may be injected directly into the subendocardial or subepicardial spaces to target afferent and/or efferent cardiac neuronal bodies and/or underlying myocardium coupled to or associated with the neuronal bodies. Alternatively, and as described below, the infusion device 410 may incorporate a sharp tip to enable puncturing cardiac tissue and creating a passage through the myocardium.

Surgical access to the inter-ventricular septum and/or ventricular free wall may be obtained through available surgical access during concomitant open or minimally invasive surgical access for another surgical procedure or as a stand-alone procedure to administer the reinnervation materials and/or fluid solution(s). If the heart is stopped during cardiopulmonary bypass procedures, then the reinnervation materials and/or fluid solutions may be injected under direct or endoscopic visualization directly into the inter-ventricular septum and/or ventricular free wall endocardium through the available heart wall incision(s). During beating heart surgeries, a needle with or without guiding sheath support may be directly inserted through the epicardium at the right ventricular insertion points and/or ventricular free wall, as shown in FIG. 4B, to inject reinnervation materials and/or fluid solution(s).

Injecting reinnervation materials and/or fluid solutions(s) into the inter-ventricular septum may alternatively be achieved percutaneous catheterization by passing and/or steering a guiding catheter through the right atrium, past the tricuspid valve, into the right ventricle, and into engagement with ventricular septum, as shown in FIG. 3. A needle with or without integrated guidewire 410 can penetrate the right ventricular endocardium so the reinnervation materials and/or fluid solution(s) 10 may be injected into the inter-ventricular septum. An injection guidewire 410 can be inserted through the needle 440 into the septum to provide stable access for longer injection of the reinnervation materials and/or fluid solution(s).

To percutaneously access His-Purkinje system components associated with the left ventricular free wall, a transeptal puncture between the right and left atria at the fossa ovalis enables passing a sheath into the left atrium. A guiding catheter 400 may be passed through a transeptal sheath and advanced and/or steered through the mitral valve and into engagement with the left ventricular endocardium. A needle with or without an injection guidewire can be used to penetrate the endocardium and transfer reinnervation materials and/or fluid solution(s) 10 into the myocardium associated with the His-Purkinje system components. This may also be used to deliver reinnervation materials and/or fluid solution(s) to cardiac intrinsic nervous system, as discussed previously. Variations of devices are discussed below, where these devices can be used to access and inject injecting reinnervation (or denervation) materials and/or fluid solution(s) into the ventricular septum and/or ventricular free wall during percutaneous transeptal, other catheter-based, open surgical, and/or minimally invasive surgical (e.g., endoscopic, thoracoscopic, subxiphoid) procedures.

Surgical or percutaneous catheter-based embodiments of the invention may also be utilized to inject reinnervation materials and/or fluid solution(s) into fat pads associated with the coronary arteries, shown in FIG. 2B, to target ganglia, cardiac intrinsic nervous system, and/or other neuronal bodies that traverse adjacent the coronary arteries and veins. Surgical access, including subxiphoid pericardiocentesis, subxiphoid pericardial window, thoracoscopy, thoracotomy, median sternotomy, or other extracardiac approach, enables directly inserting a needle 440 with or without integrated infusion guidewire 410 into the fat pads, as shown in FIG. 2B, such that reinnervation (or denervation) materials or fluid solution(s) may be injected into the fat pads that house the ganglia, cardiac intrinsic nervous system, and/or neuronal bodies under direct or endoscopic visualization.

Percutaneous catheter-based access to the fat pads that traverse the coronary arteries and veins may be achieved by inserting and/or steering a guiding catheter into the coronary sinus to target fat pads along the annulus adjacent to the circumflex, into the great coronary vein to target fat pads associated with the left anterior descending artery, and into the right coronary vein to target fat pads associated with the right coronary artery. After accessing the coronary veins with a guiding catheter 400, a needle 440 may be advanced through the venous wall into the extravascular space encapsulated by the fat pads, as shown in FIG. 2B. The needle 440 may be used or may alternatively provide a conduit to advance a guidewire 410 containing a lumen to inject reinnervation materials and/or fluid solution(s) into the extravascular fat pad space containing ganglia, cardiac intrinsic nervous system and/or neuronal bodies.

Percutaneous catheter-based embodiments, which may also be utilized during surgical access described above, as shown in FIG. 4A, provide a guiding catheter that can be inserted intravascular (or extravascular for surgical access above) and manipulated to the desired location. FIG. 5 illustrates an example of a guiding catheter or sheath 400 for use in delivering the reinnervation substances 10. The guiding catheter 400 can include a steering mechanism or actuator 402 to facilitate maneuvering the distal end 430 of the device 400 to an optimal location. While FIG. 5 shows a wheel-type steering mechanism 402, any steering actuator 402 can be used by the device (e.g., lever, slider, etc.) The steering mechanism can be wire-based or advance a shaft or tube within the device shaft 406. It is understood that any steering mechanism known in with steerable devices/catheters can be used in the variations of the devices 400 described herein. In addition, steering of the device 400 can include a ratchet-type effect to position the working end or distal tip 430 in a desired profile. In addition, the catheter 400 can include an injection needle that is advanceable therethrough. In an alternate variation, the needle can remain within the device 400 and is fluidly coupled to a source of substances 10 by a hub 412 having a tubing 414 that extends through the device 440 to be in fluid communication with the needle. Optionally, the needle 410 can advance using an advancement feature 404 (e.g., slider, wheel, lever, etc.). In additional variations, the injection needle 410 comprises guidewire with a lumen. The guiding catheter 400 may alternatively include a balloon or other stabilization structure (e.g., expandable spline, umbrella, or other structure) along a shaft 406 or at the articulation portion 408 to maintain position while the small diameter, elongated needle/guidewire 410 is advanced through the vessel wall into the desired location where the reinnervation or denervation fluid solution(s) can be injected directly or through a separately inserted injection guidewire 410. Variations of the shaft 406 can include a flexible shaft 406 that is able to navigate tortuous vascular anatomy to reach the targets of interest in the heart. Alternatively, variations of the device include shaft 406, that is rigid for those procedures performed through ports or open surgery. The articulation portion 408 can be configured to steer in an arcuate/curved manner or simply deflect away from an axis of the shaft 406.

Percutaneous catheter-based devices 400 that access the ganglionated plexi, cardiac intrinsic nervous system, other neuronal bodies, and/or underlying cardiac tissue associated with the pericardial reflections use a guiding catheter 400 for passage into the right atrium, and a needle 410 to puncture the interatrial septum below the fossa ovalis to access the epicardial space between the right and left atria below the septum to access the cavity encapsulated by the pericardial reflections, as shown in FIG. 4A into which the injected reinnervation (or denervation) solution 100 can fill the entire pericardial reflection cavity and produce the desired reinnervation (or denervation) response, as shown in FIG. 4B. Additional variations may further include a guidewire configuration with an injection lumen that may be inserted through a needle to pass into the pericardial reflection cavity and provide a more stable access site through which the reinnervation (or denervation) solution 10 can be injected.

Figure 6A:
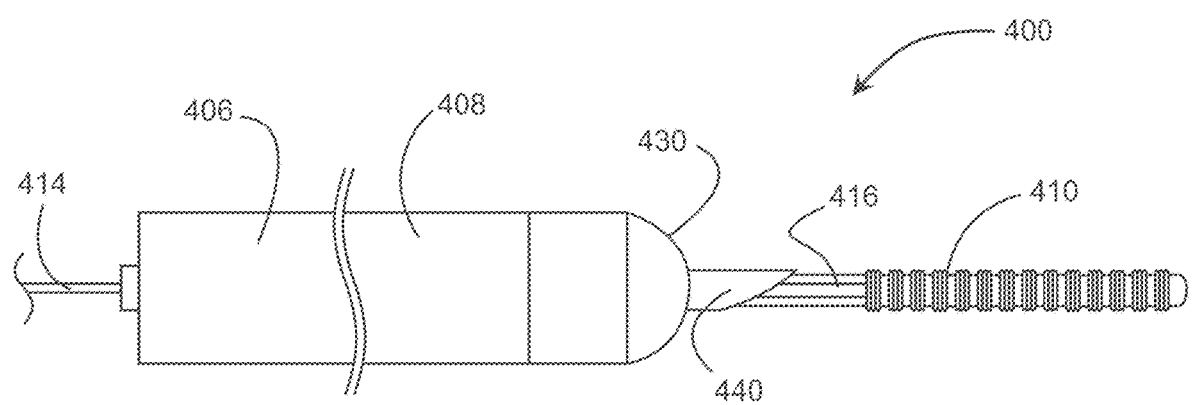
FIG. 6A shows a variation of a surgical device that incorporates an infusion guidewire that contains a lumen to permit injection of reinnervation (or denervation) materials and/or other fluid solution(s).
Figure 6B:
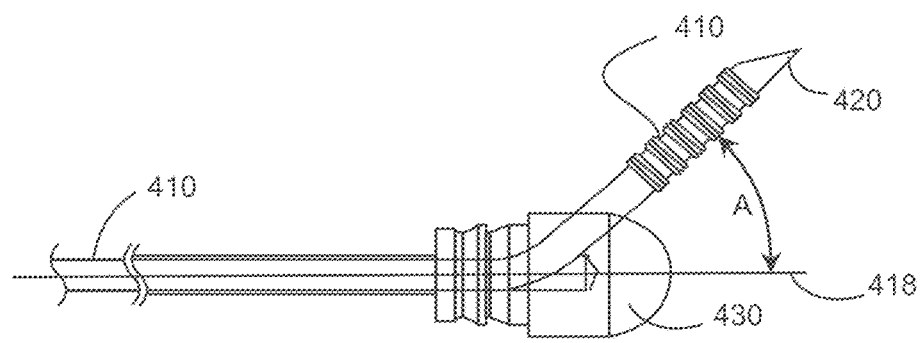
FIGS. 6B to 6D illustrate variations of a tip or distal element of the devices described herein.
Figure 6C:
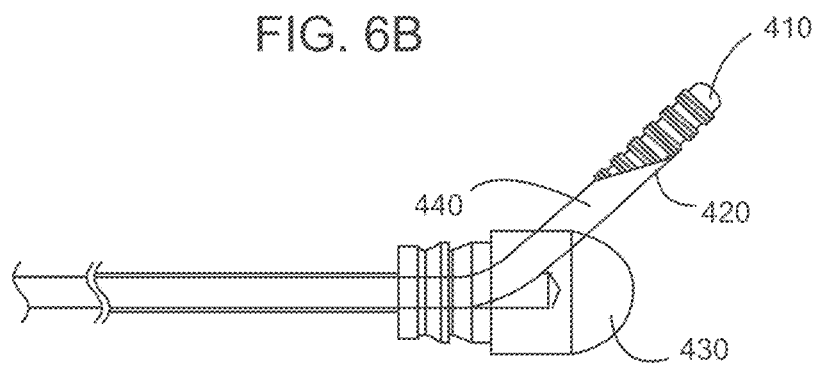

FIGS. 6A to 6C show a number of variations of a distal section 430 of the device 400 shown in FIG. 5. FIG. 6A shows a variation of a surgical device 400 that incorporates an infusion guidewire 410 that contains a lumen 416 to permit injection of reinnervation (or denervation) materials and/or other fluid solution(s) into the cavity defined by the pericardial reflections as described above. The infusion guidewire 410 can include a central lumen 416 to inject reinnervation or denervation materials and/or other fluid solution(s) through an end opening, pores through the side wall of the guidewire, and/or openings between the helically wound coils of the guidewire, or a combination thereof. In FIG. 6A, the guidewire 410 passes through a central lumen of the device 400 and extends axially beyond the distal end. FIG. 6A also illustrates a piercing member or additional needle 440 through which the guidewire 410 can advance.

Figure 6D:
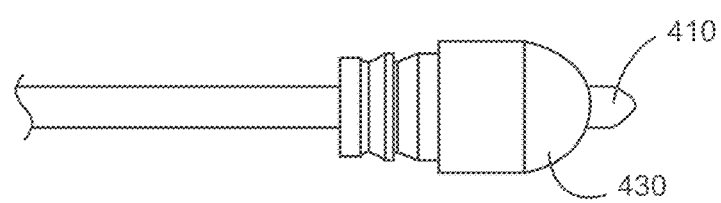

FIGS. 6B and 6C illustrate variations of a tip or distal element 430 of the devices 400 described herein. It is noted that any variation shown in the various figures can be combined with alternate variations shown in alternate figures. For example, FIG. 6B illustrates the guidewire 410 having a sharpened tip 420 to permit penetration of tissue and allow substances passing through the guidewire lumen (e.g., 416 in FIG. 6A) to pass into tissue. The guidewire 510 of FIGS. 6A and 6C pass out of the tip 430 at an angle A relative to an axis 418 of the articulation portion 408/shaft 406. In FIG. 6C, the guidewire 410 passes through a piercing device (e.g., a needle) 440, which can be stationary or advanceable relative to the distal element 430 and/or the guidewire 410. FIG. 6D illustrates the guidewire 410 passing through the tip 430 through the distal end of the tip 430.

While not shown, the guidewire 410 described herein can be configured to have an atraumatic tip such as a J-hook or other flexible profile or other atraumatic design to enable passing within the cavity defined by the pericardial reflections to target regions within the pericardial reflections that enable targeting specific regions where neuropathies or damage of underlying myocardium have been mapped during electrophysiology procedures or non-invasive imaging exams. Alternatively, the guidewire may be manipulated to ensure the entire cavity defined by the pericardial reflections is filled with reinnervation or denervation materials and/or other fluid solution(s).

The guidewire 410 in the variations shown in FIGS. 10E to 10G include a sharp distal tip 420 and may also include a pre-shaped curvature such that when straightened in the distal element 430 it can puncture through atrial tissue adjacent to the fossa ovalis or along the cavity defined by the pericardial reflections. Once the guidewire 410 is advanced into the cavity defined by the pericardial reflections, it assumes a curved orientation to reduce the potential for abrading or puncturing tissue to enable atraumatically infusion reinnervation or denervation materials and/or other fluid solution(s).

As shown in those variations that include a separate but integrated needle or piercing structure 440 (e.g., FIGS. 6A, 6C), the needle 440 creates access through the atrium into the cavity defined by the pericardial reflections such that a separate guidewire 410 can be inserted through the central lumen of the needle 440 until it enters the cavity defined by the pericardial reflections. Once the needle 440 punctures atrial tissue and access the cavity defined by the pericardial reflections, the guidewire 410 advances through the needle 440 such that the distal section of the guidewire is positioned within or adjacent to the cavity. After positioning the guidewire 410 within the cavity defined by the pericardial reflections, the needle 440 can be retracted to remove any sharp tip within the catheter or endoscopic system to reduce abrasion or unwanted damage to the atrial wall.

Figure 7A:
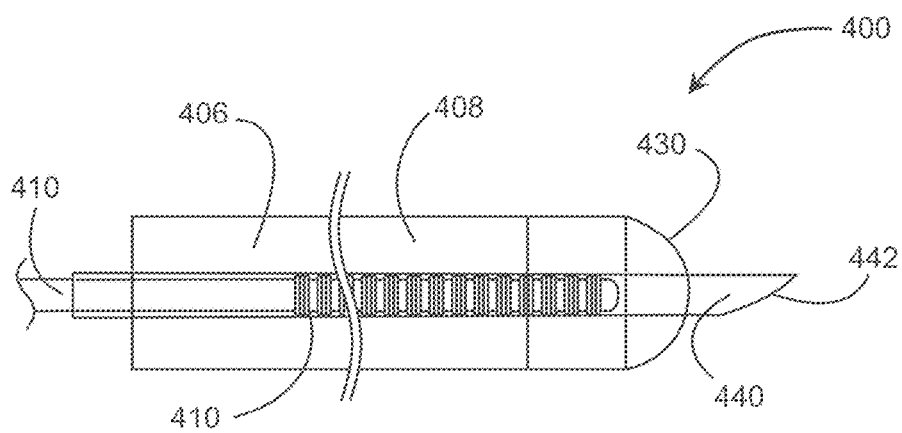
FIG. 7A illustrates an additional variation of a distal section of a variation of a device as described herein.
Figure 7B:
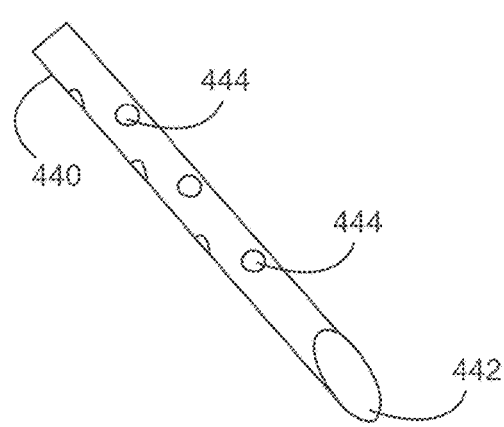
FIGS. 7B to 7E illustrate additional variations of needles for use with the device.
Figure 7C:
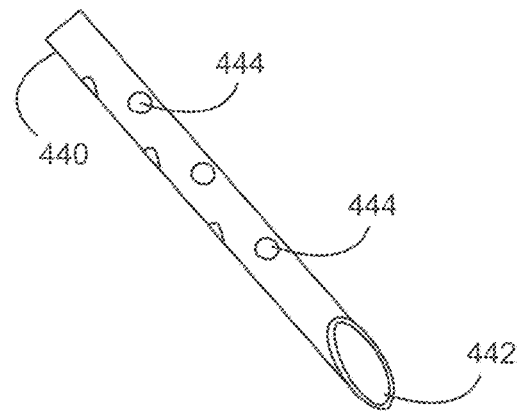
Figure 7D:
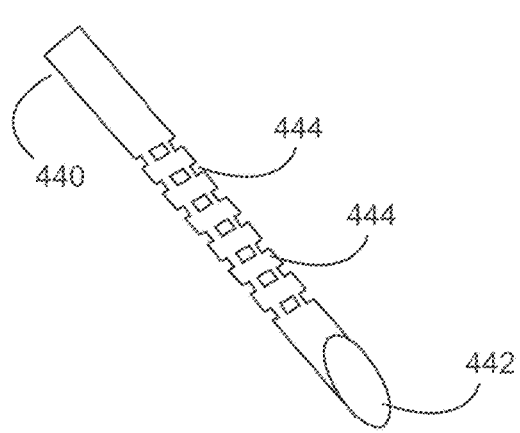
Figure 7E:
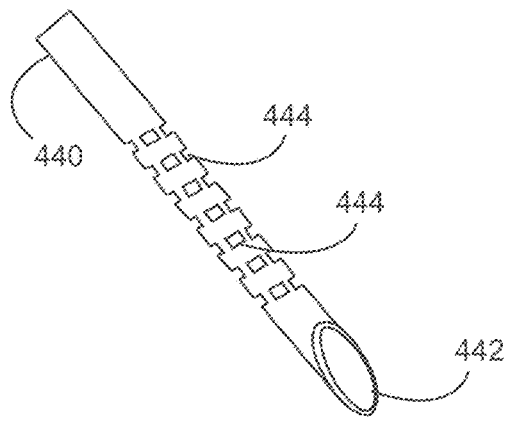

FIG. 7A illustrate an additional variation of a distal section 430 of a variation of a device 400 as described herein. As noted, the device 400 can include an infusion needle 440, with or without a guidewire 410, to inject reinnervation (or denervation) materials and/or other fluid solution(s) into the cavity defined by the pericardial reflections as described above. In this variation, a needle 440 is used to puncture atrial tissue to access the cavity defined by the pericardial reflections and is partially advanced such that reinnervation (or denervation) materials and/or other fluid solution(s) can be infused through an opening 442 at the distal end of the needle 440 or through sidewall openings 444 in a wall of the needle 440 as shown in FIGS. 7B to 7C. In addition, the needle 440 can comprise a solid/closed end, as shown in FIGS. 7B and 7D, or can have an open end at the tip, as shown in FIGS. 7C and 7E.

The surgical devices 400 described herein can also be utilized for other percutaneous catheter and/or surgical procedures associated with neuronal bodies and/or underlying tissues not located within the cavity defined by the pericardial reflections. These neuronal bodies, underlying and associated tissues, or myocardium directly or indirectly coupled to or associated with the cardiac intrinsic nervous system may be located within the ventricles (e.g., His-Purkinje System), within fat pads associated with the coronary vasculature, within adipose tissue along the epicardium, located along the exterior of the peripheral vasculature where neuronal bodies known to affect sympathetic, parasympathetic, or sensory functions reside, and/or other regions of the body where neuropathies are known to develop and/or where underlying tissues coupled to or associated with neuronal bodies can become impaired.

Figure 8:
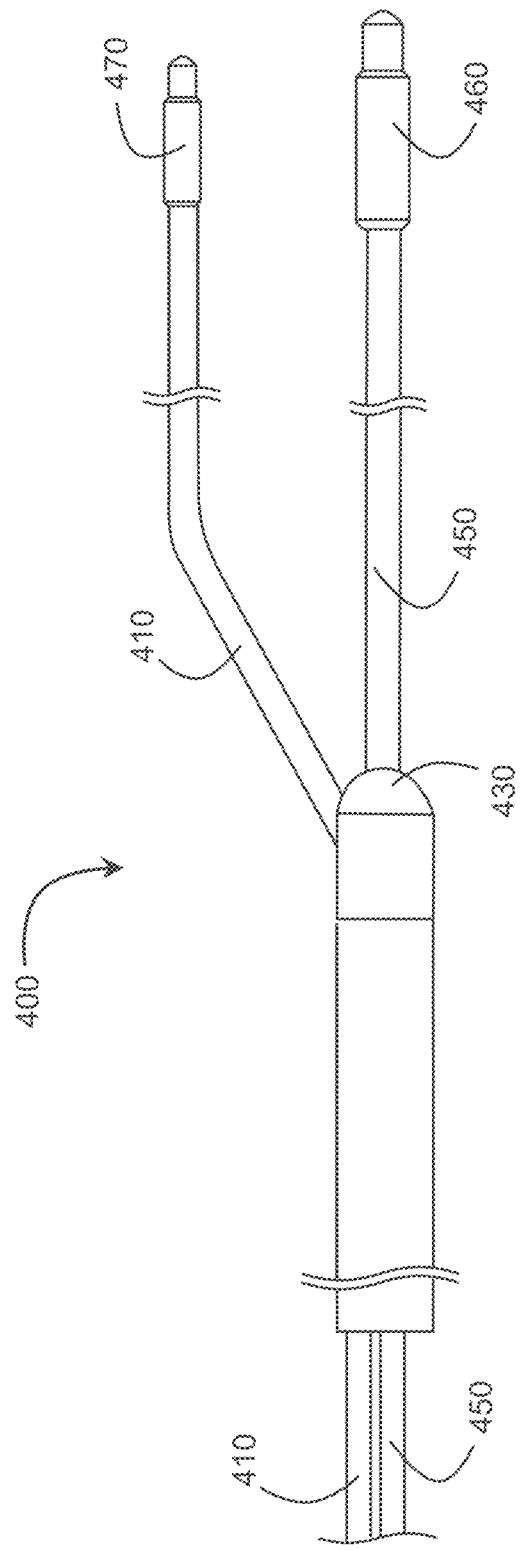
FIG. 8 illustrates a variation of a device having intravascular and extravascular members with optional magnetic features for improved delivery of reinnervation (or denervation) materials and/or other fluid solution(s).

FIG. 8 illustrates an additional variation of the device 400 described herein. In this variation, two elongate members, 410 and 450, are coupled together to enable advancing the needle and/or associated guidewire(s) through the coronary venous (or arterial) vasculature to traverse along epicardial fat pads oriented along the coronary vasculature. In one variation, elongate member 450 is configured for intravascular passage within the coronary vein or artery, while a distal separator 430 redirects the second elongate member 410 that can puncture the vessel to advance in an extravascular manner past the vessel wall into fat pads oriented along the coronary vasculature. The elongate members 410 and 450 can be visible with fluoroscopy to facilitate orientation of the second extravascular elongate member 410 relative to the first intravascular elongate member 450 to ensure proper positioning before infusion reinnervation or denervation materials and/or fluid solution(s).

One or both of the elongate members 410 and 450 can optionally include magnetic materials or magnetic features 460 & 470. When the magnetic features are activated, magnetic attraction occurs between the intravascular elongate member 450 and the extravascular elongate member 410 to ensure infusion of reinnervation or denervation materials and/or fluid solution(s) within fat pads where target neuronal bodies and/or underlying damaged myocardial tissue resides.

The variations of the devices shown herein can be used to treat extracardiac neuropathies that impact diseases such as uncontrolled arterial hypertension by injecting reinnervation (or denervation) materials and/or fluid solution(s) into extravascular fat pads, cavities, and/or regions associated with ganglia known to affect the sympathetic, parasympathetic system (e.g. celiac ganglia, superior mesenteric ganglion, aorticorenal ganglia, carotid ganglia, etc.).

The present disclosure also includes processes and methods for eliminating or preventing atrial fibrillation, or reversing effects of malignant arterial hypertension, diabetes mellitus, cardiomyopathies, inflammatory diseases, or other disease that affects cardiac function by reversing neuropathies associated with neuronal bodies within the pericardial reflection space by correcting cardiac neuropathies of ganglionated plexi, cardiac intrinsic nervous system, or other nerve bodies along the epicardial atria in the extracardiac space outlined by the pericardial reflections that connect the pericardium to the atrium. The reinnervation materials and/or fluid solution(s) may be injected into fat pads outside the heart that contain ganglia or other neuronal bodies in which neuropathies impact afferent and/or efferent signals that impact cardiac function and performance. The reinnervation materials and/or fluid solution(s) may alternatively be injected into fat pads associated with the coronary arteries along which cardiac intrinsic nervous system components reside. Neuropathies associated with the vagal nervous system or other neuronal bodies may be treated by injecting reinnervation materials and/or fluid solution(s) into the myocardium, including the His-Purkinje system, coupled to or associated with the neuronal bodies and/or into the cavity defined by the pericardial reflections. In these applications, materials and/or fluid solution(s) that induce angiogenesis, reduce inflammation, reduce oxidative stress, promote healing otherwise correct neuropathies, or improve the function of underlying tissues coupled to or associated with neuronal bodies are injected through the surgical or percutaneous intravascular devices into defined extracardiac spaces and/or intracardiac anatomy associated with the ganglia, cardiac intrinsic nervous system or other nerve bodies such that the reinnervation materials and/or fluid solution(s) do not wash out and remain around the ganglia, cardiac intrinsic nervous system, other nerve bodies, and/or underlying tissue coupled to or associated with neuronal bodies for a prolonged period of time to maximize the effect of reinnervation processes.

In similar ways shown for reinnervation described above, denervation by injecting ablative solutions in fat pads, extracardiac space, or other enclosed space(s) associated with the ganglia may alternatively be performed when reinnervation is not feasible nor effective. In the case of denervation, the nerves and/or underlying tissues coupled to or associated with the neuronal bodies are rendered inactive by ablative solutions, so uncontrolled, erratic, or atypical activation is inhibited, thereby reducing the physiologic effects of such irregular function.

It is to be understood that the present invention is by no means limited to the particular constructions herein disclosed and/or shown in the drawings but also comprise any modifications or equivalents within the scope of the invention. Although the present inventions have been described in terms of the preferred embodiments above, numerous modifications and/or additions to the above-described preferred embodiments would be readily apparent to one skilled in the art. It is intended that the scope of the present inventions extends to all such modifications and/or additions and that the scope of the present inventions is limited solely by the claims of the invention.

As for other details of the present invention, materials and manufacturing techniques may be employed within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described, and equivalents (whether recited herein or not included for the sake of some brevity) may be substituted without departing from the true spirit and scope of the invention. Also, any optional feature of the inventive variations may be set forth and claimed independently or in combination with any one or more of the features described herein. Accordingly, the invention contemplates combinations of various aspects of the embodiments or combinations of the embodiments themselves, where possible. Reference to a singular item includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments or the embodiments themselves can be combined. Where such combinations are intended to be within the scope of this disclosure.

What is claimed is:

1. A method for reversing neuropathies associated with a heart, the method comprising:
    advancing a piercing structure within a body of a patient and towards the heart;
    positioning the piercing structure adjacent to an interatrial septum of the heart and penetrating a right atrium of the heart with the piercing structure at a location adjacent to interatrial septum to access a cavity encapsulated by one or more pericardial reflections of the heart; and
    delivering a reinnervation material through the piercing structure to fill the cavity encapsulated by the one or more pericardial reflections.

2. The method of claim 1, wherein advancing the piercing structure within the body of the patient comprises navigating a tubular member into the body and advancing the piercing structure through the tubular member.

3. The method of claim 1, where positioning the piercing structure comprises penetrating at least one pericardial reflection.

4. The method of claim 1, further comprising delivering the reinnervation material through the piercing structure into the myocardium.

5. The method of claim 1, further comprising advancing a second elongate structure within a vessel and delivering the reinnervation material through both the piercing structure within the heart and through the second elongate structure on an exterior of the heart.

6. The method of claim 1, wherein the reinnervation material is selected from a group consisting of platelet rich plasma, stem cells, exosomes, extracellular vesicles, growth factors, hydrogels, hormones, human microvascular extracellular matrix tissue, microvascular tissue fragments, allograft, autograft, xenograft, anti-inflammatories, and steroids.

* * * * *